US009586030B2

(12) United States Patent
Rizq et al.

(10) Patent No.: US 9,586,030 B2
(45) Date of Patent: Mar. 7, 2017

(54) FUGITIVE PLASTICIZER BALLOON SURFACE TREATMENT FOR ENHANCED STENT SECUREMENT

(75) Inventors: Raed Rizq, Fridley, MN (US); John J. Chen, Plymouth, MN (US); Stanley Nordin, Monticello, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2823 days.

(21) Appl. No.: 11/022,585

(22) Filed: Dec. 23, 2004

(65) Prior Publication Data

US 2006/0142834 A1 Jun. 29, 2006

(51) Int. Cl.

*A61F 2/06* (2013.01)
*A61M 25/10* (2013.01)
*A61F 2/958* (2013.01)

(52) U.S. Cl.

CPC ......... *A61M 25/1027* (2013.01); *A61F 2/958* (2013.01); *A61F 2002/9583* (2013.01); *A61M 2025/1088* (2013.01)

(58) Field of Classification Search

USPC ........................................................ 623/1.11
See application file for complete search history.

(56) References Cited

U.S. PATENT DOCUMENTS 2,888,350 A * 5/1959 Snyder et al. ................ 426/106
3,218,287 A * 11/1965 Schmidle et. al. ........... 524/310
3,892,905 A * 7/1975 Albert ........................... 428/220
4,733,665 A 3/1988 Palmaz ......................... 606/108
4,740,207 A 4/1988 Kreamer ...................... 623/1.15
4,950,227 A 8/1990 Savin et al. ................. 623/1.12
4,950,239 A 8/1990 Gahara et al. ............. 604/96.01
5,007,926 A 4/1991 Derbyshire .................. 623/1.15
5,026,377 A 6/1991 Burton et al. ................ 606/108
5,096,848 A 3/1992 Kawamura ................... 438/425
5,108,416 A 4/1992 Ryan et al. ................... 606/194
5,158,548 A 10/1992 Lau et al. ..................... 606/194
5,207,837 A * 5/1993 Honeycutt ...................... 134/42
5,242,399 A 9/1993 Lau et al. ..................... 604/104
5,292,331 A 3/1994 Boneau ........................ 623/1.16
5,304,197 A * 4/1994 Pinchuk et al. .............. 606/194
5,330,428 A 7/1994 Wang et al. ............. 604/103.14
5,344,426 A 9/1994 Lau et al. .................... 623/1.11
5,403,341 A 4/1995 Solar ............................ 606/198

(Continued)

FOREIGN PATENT DOCUMENTS

EP 707837 A1 4/1996
EP 1 508349 2/2005

(Continued)

OTHER PUBLICATIONS

T.L. St. Clair and H.D. Burks, "Thermoplastic/Melt-Processable Polyimides," NASA Conf. Pub. #2334 (1984), pp. 337-355.

*Primary Examiner* — Julie A Szpira
(74) *Attorney, Agent, or Firm* — Seager, Tufte & Wickhem, LLP

(57) ABSTRACT

In an assembly of a balloon mounted on a catheter and a stent mounted over the deflated balloon, the balloon is provided with a fugitive plasticizer before the stent is crimped over the balloon. The fugitive plasticizer can soften the balloon surface so that molding of the balloon surface to conform to the crimped stent occurs. The fugitive plasticizer is removed before the assembly is used.

21 Claims, 1 Drawing Sheet

(56) References Cited

U.S. PATENT DOCUMENTS 5,415,664 A 5/1995 Pinchuk ........................ 623/1.11
5,453,090 A 9/1995 Martinez et al. ............. 606/108
5,484,449 A * 1/1996 Amundson et al. .......... 606/108
5,484,565 A * 1/1996 Larsen et al. ................. 264/230
5,500,180 A 3/1996 Anderson et al. ............ 264/532
5,830,217 A * 11/1998 Ryan ............................ 623/1.11
5,836,965 A 11/1998 Jendersee et al. ........... 623/1.11
5,869,127 A * 2/1999 Zhong .......................... 427/2.12
5,951,941 A * 9/1999 Wang et al. .................. 264/523
5,968,069 A 10/1999 Dusbabek et al. ............ 606/194
5,976,181 A 11/1999 Whelan et al. .............. 623/1.12
6,017,334 A * 1/2000 Rawls ........................... 604/265
6,019,789 A 2/2000 Dinh et al. ................... 623/1.15
6,096,056 A * 8/2000 Brown .......................... 606/194
6,146,356 A 11/2000 Wang et al. ............... 604/96.01
6,187,013 B1 2/2001 Stoltze et al. ................ 606/108
6,245,076 B1 6/2001 Yan .............................. 606/108
6,348,060 B1 * 2/2002 Brown .......................... 606/194
6,464,718 B1 10/2002 Miller et al. ................. 623/1.11
6,572,813 B1 6/2003 Zhang et al. ................. 264/519
6,620,191 B1 9/2003 Svensson ..................... 623/1.11
6,666,880 B1 12/2003 Chin et al. ................... 623/1.11
6,733,520 B2 5/2004 Yang et al. .................. 623/1.12
6,776,793 B2 8/2004 Brown et al. ................ 623/1.15
7,886,419 B2 * 2/2011 Huang et al. .............. 29/407.08
2001/0014821 A1 * 8/2001 Juman et al. ................ 623/1.11
2002/0095208 A1 7/2002 Gregorich et al. .......... 623/1.15
2003/0083732 A1 5/2003 Stinson ........................ 623/1.15
2003/0083736 A1 5/2003 Brown et al. ................ 623/1.16
2004/0213933 A1 * 10/2004 Varma .......................... 428/36.9
2006/0134357 A1 * 6/2006 Godaire et al. .............. 428/35.2

FOREIGN PATENT DOCUMENTS

WO WO 96/03092 2/1996
WO WO 9836783 A1 * 8/1998 ............. A61L 29/00

* cited by examiner

A

B

FUGITIVE PLASTICIZER BALLOON SURFACE TREATMENT FOR ENHANCED STENT SECUREMENT

FIELD OF THE INVENTION

The present invention relates to balloons for catheters used in medical stent delivery, to catheter/stent assemblies having such balloons and to processes for making the balloons.

BACKGROUND OF THE INVENTION

Stents and stent delivery assemblies are utilized in a number of medical procedures and situations, and as such their structure and function are well-known. Intraluminal stents are used to maintain the patency of blood vessels and other body lumens. Use of stents to keep open a coronary or other artery after an angioplasty procedure has been performed is now a common practice. Stents are also commonly used in the treatment of urological disorders.

Stents that may be delivered to a restricted coronary artery or other body lumen, expanded to a larger diameter as by a balloon catheter, and left in place in the dilated lesion are described in many patent documents including U.S. Pat. No. 4,740,207, Kreamer; U.S. Pat. No. 5,007,926, Derbyshire; U.S. Pat. No. 4,733,665, Palmaz; U.S. Pat. No. 5,026,377, Burton, et al; U.S. Pat. No. 5,158,548, Lau, et al; U.S. Pat. No. 5,242,399, Lau, et al; U.S. Pat. No. 5,292,331, Boneau; U.S. Pat. No. 5,344,426, Lau, et al; U.S. Pat. No. 5,415,664, Pinchuck; U.S. Pat. No. 5,453,090, Martinez, et al; U.S. Pat. No. 4,950,227, Savin; U.S. Pat. No. 5,403,341, Solar; U.S. Pat. No. 5,108,416, Ryan, et al; EP 707837 A1, Scheiban; WO 96/03092, Medinol Ltd; U.S. Pat. No. 6,019,789, Dinh, et al; U.S. Pat. No. 6,776,793, Brown, et al; US 20020095208 A1, Goran; US 20030083732 A1, Stinson and US 20030083736 A1, Brown, et al, the entire contents of all of which are incorporated herein by reference.

In advancing a balloon expandable stent through a body vessel to the deployment site, there are a number of important considerations. The stent must be able to securely maintain its axial position on the delivery catheter. The stent, particularly its distal and proximal ends, are sometimes protected to prevent distortion of the stent, and minimize trauma to the vessel walls. Balloon expandable stent delivery and deployment assemblies are known which utilize restraining means that overlay the stent, or a portion thereof, during delivery. U.S. Pat. No. 5,968,069, Dusbabek, et al, and U.S. Pat. No. 6,733,520, Yang, et al, provide examples of such stent delivery and deployment systems.

Other methods for improving stent securement have involved modifications of the balloon/stent interface. Heated crimping, and other heat and/or pressure-based processing are known and used to improve securement, in some cases together with an accompanying chemical treatment or imposition of an intervening structure. Examples of such methods are included in U.S. Pat. No. 6,187,013, Stoltze et al; U.S. Pat. No. 5,836,965, Jendersee, et al; U.S. Pat. No. 5,976,181, Whelan, et al; U.S. Pat. No. 6,245,076, Yan; U.S. Pat. No. 6,464,718, Miller, et al; U.S. Pat. No. 6,620,191, Svensson; and U.S. Pat. No. 6,666,880, Chiu, et al.

SUMMARY OF THE INVENTION

The invention relates to balloon catheter/stent or catheter/stent assemblies and to methods for preparing same.

The applicant's have discovered that balloon or catheter materials can be sufficiently softened with a fugitive plasticizer to produce surface molding and/or improved retention when a stent is crimped thereon, even without heating or internal pressurization of the balloon. The fugitive plasticizer does not attack the balloon material, as a solvent would do. Following crimping, the fugitive plasticizer may be removed by evaporation, optionally under vacuum, again with little or no heating. Stent retention is improved with little or no affect on balloon properties.

The invention is particularly beneficial for increasing stent retention of drug-coated stents where the levels of heat needed to improve securement may negatively impact the drug/coating.

DETAILED DESCRIPTION OF THE INVENTION

Figures 1, 2:
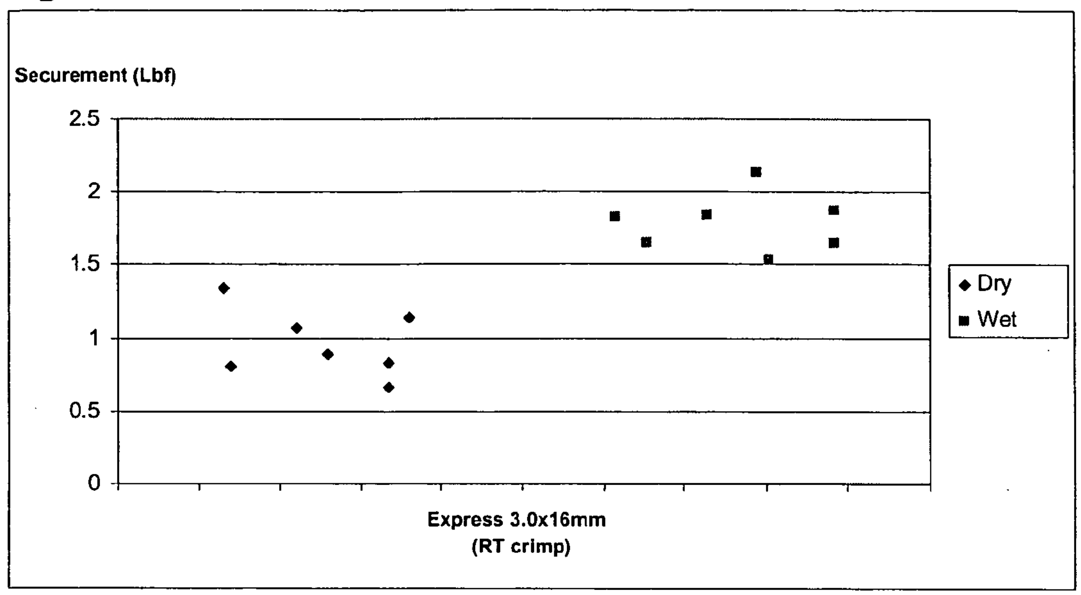
FIG. 1 is a graph of data obtained in the Example, showing relative stent retention forces obtained using control and invention balloon catheter assemblies.
FIG. 2 shows two photographic images of balloon deformation obtained from crimping a stent on a control balloon A and an invention balloon B.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

As used herein the concept of a fugitive plasticizer is a compound that can penetrate the balloon material to soften it, without dissolving the balloon material, in the manner of a traditional plasticizer, but that subsequently can be removed without melting or dissolving the balloon material or damaging an attached stent.

The fugitive plasticizer may be a material that can be absorbed into the balloon material without substantial swelling. The fugitive plasticizer may be one that will be absorbed in an amount of from about 0.1% to about 10% by weight of the balloon material, or even more, without swelling the material volume more than about 5%.

Removal of the fugitive plasticizer is typically accomplished by volatilization. Desirably removal is accomplished at a maximum temperature of about 50° C. or less, for instance at about ambient temperature. A vacuum may be applied to facilitate removal.

The balloon may be formed of any balloon polymer material for which a suitable fugitive plasticizer is available.

It is possible to make balloons from a variety of thermoplastic polymers. Materials and methods of making catheter balloons are well known. Such materials may include low, linear low, medium and high density polyethylenes; polypropylenes; poly(ethylene vinyl acetate) (EVA); poly(ethylene vinyl alcohol) (EVOH) and EVA/EVOH terpolymers; polyolefin-ionomers; ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; polyesters and copolyesters; polycarbonate; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); and PES (polyether sulfone). Physical blends and copolymers of such materials may also be used.

Orientable polyesters, especially polyethylene terephthalate (PET), may be used for forming catheter balloons. Suitable PET polymers have an initial intrinsic viscosity of at least 0.5, for instance, 0.6-1.3. Other high strength polyester materials, such as poly(ethylene napthalenedicarboxylate) (PEN); and poly(butylene terephthalate may also be used. Polyester copolymers such as the random copolymer made from dimethyl terephthalate dimethyl isophthalate and ethylene glycol described in U.S. Pat. No. 5,330,428 Wang, et al., may also be employed.

Examples of polyamides which may be used include nylon 6, nylon 64, nylon 66, nylon 610, nylon 610, nylon 612, nylon 46, nylon 9, nylon 10, nylon 11, nylon 12, and mixtures thereof.

The balloon may be formed of polyurethanes such as Tecothane® from Thermedics. Tecothane® is a thermoplastic aromatic polyether polyurethane synthesized from methylene diisocyanate (MDI), polytetramethylene ether glycol (PTMEG) and 1,4 butanediol chain extender. Tecothane® 1065D and 1075D are examples. Other polyurethanes which have been used are Isoplast® 301, a high strength engineering thermoplastic polyurethane, and Pellethane® 2363-75D, both sold by Dow Chemical Co. References illustrating polyurethane balloon materials include U.S. Pat. No. 4,950,239, to Gahara, U.S. Pat. No. 5,500,180 to Anderson et al, U.S. Pat. No. 6,146,356 to Wang, et al., and U.S. Pat. No. 6,572,813, to Zhang, et al.

Other suitable polymeric materials include Engage® from DuPont Dow Elastomers (an ethylene alpha-olefin polymer) and Exact®, available from Exxon Chemical, both of which are thermoplastic polymers and are believed to be polyolefin elastomers produced from metallocene catalysts. These are compliant materials which provide balloons which have a substantial range of available diameters to which they may be expanded and still recover elastically.

Balloons of the invention may be also made of polyamide/polyether block copolymers. The polyamide/polyether block copolymers are commonly identified by the acronym PEBA (polyether block amide). The polyamide and polyether segments of these block copolymers may be linked through amide or ester linkages, especially polyamide/polyether polyesters. Polyamide/polyether polyesters are sold commercially under the Pebax® trademark by Elf Atochem North America, Inc., Philadelphia Pa. Examples of suitable commercially available polymers are the Pebax® 33 series polymers with hardness 60 and above, Shore D scale, especially Pebax® 6333, 7033 and 7233. These polymers are made up of nylon 12 segments and poly(tetramethylene ether) segments.

It is also possible to utilize polyester/polyether segmented block copolymers. Such polymers are made up of at least two polyester segments and at least two polyether segments. The polyether segments are the same as previously described for the polyamide/polyether block copolymers useful in the invention. The polyester segments are polyesters of an aromatic dicarboxylic acid and a two to four carbon diol. The polyether segments of the polyester/polyether segmented block copolymers are aliphatic polyethers having at least 2 and no more than 10 linear saturated aliphatic carbon atoms between ether linkages. More preferably the ether segments have 4-6 carbons between ether linkages, and most preferably they are poly (tetramethylene ether) segments. Examples of other polyethers which may be employed in place of the preferred tetramethylene ether segments include polyethylene glycol, polypropylene glycol, poly(pentamethylene ether) and poly (hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1000.

The polyester segments are polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids. Preferred polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel® 8230.

Examples of thermoplastic polyimides are described in T. L. St. Clair and H. D. Burks, "Thermoplastic/Melt-Processable Polyimides," NASA Conf. Pub. #2334 (1984), pp. 337-355. A suitable thermoplastic polyimide is described in U.S. Pat. No. 5,096,848 and is available commercially under the tradename Aurum® from Mitsui Toatsu Chemicals, Inc., of Tokyo, Japan.

Fugitive plasticizers for coatings, films, floor polishes, polymer emulsions and molding compositions are well known. In some embodiments, the fugitive plasticizer is a solar organic compound or water.

Typical compounds include polyhydric alcohols, e,g, ethylene glycol, propylene glycol, diethylene glycol and dipropylene glycol; mono- and di-alkyl glycol ethers, e.g. $C_1$-$C_6$ mono and di alkyl ethers of ethylene glycol, propylene glycol, diethylene glycol or dipropylene glycol; acetate esters of glycol monoalkyl ethers, e.g. ethylene glycol monomethyl ether acetate, ethylene glycol monobutyl ether acetate and diethylene glycol monobutyl ether acetate; isophorone; benzyl alcohol; 3-methoxybutanol-1; 3-methoxybutanol-3; ethylene carbonate; propylene carbonate; phenylglycol ethers; and 2,2,4-trimethyl-1,3-pentanediolmonoisobutyrate. Phenols and dihydroxybenzenes, e.g. phenol and resorcinol, have been reported to function as fugitive plasticizers. These compounds can also be used as fugitive plasticizers in the present invention. Mixtures of any of these compounds can also be used. Compounds or mixtures of compounds that can solubilize the polymer only at elevated temperatures, for instance above about 120° C., may function as suitable fugitive plasticizers at or near ambient temperature.

The fugitive plasticizer may be a compound that is a liquid at ambient temperature and pressure and has a boiling point at standard pressure of from about 95° C. to about 200° C.

For balloon materials that undergo substantial inter-polymer hydrogen bonding, such as polyamides, polyurethanes, and block copolymers comprising polyamide or polyurethane blocks, a suitable fugitive plasticizer is water. Water is particularly desirable as it needs only to be removed to the equilibrium level obtained under ambient temperature and pressure conditions, a step that can be accomplished simply by storage.

The amount of fugitive plasticizer to be incorporated into the balloon polymer material is an amount that is effective to soften the polymer. The amount may be in excess of the ambient equilibrated amount, i.e., the amount that remains in the polymer material after extended equilibration at ambient temperature, humidity and pressure.

According to one exemplary method of practicing the invention the balloon mounted on a catheter is immersed in a bath of liquid fugitive plasticizer for an extended period, typically more than several hours, for instance a day or longer. Preferably the time is sufficient to establish saturation. Suitable saturation time can be established by testing weighed samples of balloon material at successive intervals until the balloon samples do not noticeably gain further weight if the immersion time is doubled. Desirably the temperature of the liquid fugitive plasticizer bath is maintained at no more than 50° C., preferably at a temperature of from about ambient to body temperature (37° C.). In some cases the fugitive plasticizer will not attack the catheter material so that the entire balloon catheter assembly can safely be immersed in the fugitive plasticizer bath. In some cases the fugitive plasticizer bath may be pressurized to facilitate absorption of the fugitive plasticizer.

Alternatively the balloon may be treated with concentrated vapor of the fugitive plasticizer. In some cases pressure may be employed in a vapor treatment step to facilitate penetration of the fugitive plasticizer into the balloon material.

The balloon may be treated with the fugitive plasticizer before or after the balloon is deflated and folded around the catheter. The stent is then crimped over the folded balloon. These steps are performed in conventional manner. If the fugitive plasticizer is water, no special further treatment is needed. Under normal storage and handling conditions absorbed water in the balloon wall will evaporate until equilibrium is established with ambient humidity is established, so that the water content in the balloon at shipment for use will not be significantly different from that found in balloons that have not undergone processing in accordance with the invention.

If an organic compound is used as a fugitive plasticizer, ambient equilibration may be a suitable removal step in some instances. In other instances additional steps may be needed to facilitate expeditious removal. Subjecting the assembly to a vacuum can be employed to remove the fugitive plasticizer after the stent has been crimped onto the balloon. Water, of course, can also be removed more expeditiously under vacuum. Lowering temperature to decrease polymer/plasticizer compatibility may also facilitate removal of the fugitive plasticizer.

In some cases extraction of the fugitive plasticizer may be feasible if a solvent for the plasticizer exists that does not attack the balloon, the stent and/or the catheter. Water can be an effective extraction solvent for many of the alcohols, alcohol ethers, and other organic compounds previously identified as potential fugitive plasticizers.

In the case that the fugitive plasticizer comprises a compound other than water, it is desirable that it be removed to an amount of less than 0.1% by weight of the balloon polymer material.

Because the crimping process occurs before the plasticizer is removed, the balloon material is softened and deforms to conform to the contacting surfaces of the stent to a greater degree than is found when only crimping is employed. This surface deformation is retained even after the fugitive plasticizer is removed, so that the force necessary to displace the stent from the balloon is higher than is obtained for a stent crimped over an untreated balloon. Moreover, because the plasticizer is fugitive, in at least some embodiments, there will be no significant difference in wall strength between treated and untreated balloons. The distension profile of the balloon, however, should be determined on balloons treated with the fugitive plasticizer, in case there is some effect on the balloon inflation properties.

In at least some embodiments of the invention it is not necessary to pressurize the balloon to conform it to the stent. The balloon is softened before the stent is crimped, so the crimping action alone can be effective to reform the balloon surface. This can be done at ambient temperature. It should be understood, however, that the use of elevated temperatures and/or balloon pressurization may be appropriate additional steps for the practitioner without departing from the invention. If employed, such steps may be performed after crimping, as in prior art surface reformation techniques, or they may be concurrently with the crimping step.

The balloon material may be multilayered, in which case the fugitive plasticizer should plasticize at least the outer layer, not dissolve the inner layer(s), and not attack the boundary between the two layers.

Any conventional type of balloon catheter suited for stent delivery may be used, such as a catheter of the type generally used for PTA or PTCA angioplasty procedures, for prostate therapy, and TTS endoscopic catheters for gastrointestinal use. The invention can be used with fixed wire, over-the-wire and single operator exchange assemblies. Suitable catheters that may be used in stent delivery assemblies include a number of catheters available from Boston Scientific Corporation, such as the BANDIT™, COBRA™, VIVA™, VIVA PRIMO™, MAXXUM™, MAXXUM ENERGY™ RANGER™ MAVERICK™ catheters.

A stent for use according to the present invention may be any conventional type of balloon expandable stent, including stents of the type used for PTA and PTCA angioplasty procedures, for prostate therapy, and TTS endoscopic catheters for gastrointestinal use. Suitable stent material is biocompatible stainless steel in the form of sheet metal, tube component or wire. Titanium and titanium alloys such as Nitinol, and other metal alloys, can also be used. The stent should be at least partially balloon expandable. Balloon expandable polymer stents may be used. Particular examples of suitable stents available from Boston Scientific Corporation include the EXPRESS™, EXPRESS-2™, LIBERTE™, SENTINOL™ and NEUROFORM™ stents. Other suitable stents are described in the Background section, above.

The stent may have a coating, for instance a coating that releases a drug such as paclitaxel. Stents having such a drug coating are known, and include the TAXUS™ stent products available from Boston Scientific Corporation. The low heat and solvency requirements of the present invention may be particularly advantageous with coated stents since there is less likelihood of damage to the coating or the drug from the fugitive plasticizer, as compared to techniques that employ solvents, or heating of the balloon and stent, or both, to soften a balloon.

In use the balloon catheter/stent assemblies of the invention are delivered by standard techniques to the deployment site within the body vessel of interest. At this point, stent is positioned as required by the physician and balloon is fluid inflated by standard technique to expand stent to its deployment diameter. During this expansion, the stent is expanded to fill the body vessel. Following deployment of the stent, the balloon is deflated and the assembly is retracted proximally and withdrawn from the body. If required by the procedure, the site of entry to the body is appropriately closed.

The invention is illustrated by the following non-limiting Example

Example

A quantity of 14 balloon catheters, substantially as manufactured and sold by Boston Scientific Corporation with the Express-2® stent delivery system were used in this Example. The balloons of these catheters were formed of Pebax® 7233 and were 3.0 mm diameter×16 mm long. The stents were Express® stainless steel stents, also manufactured and sold by Boston Scientific Corporation. A batch of seven catheters and stents was used for the invention example and compared to a control batch of seven catheters and stents.

For the invention batch the entire catheters were pre-soaked in 37° C. water for 13 hours. After removing, and drying the catheters with paper towelettes, the stents were crimped at room temperature. No water soaking step was used with catheters of the control batch. The control batch stents were simply mounted directly on the balloons. The crimping pressure and protocol was the same for both batches of catheters.

Each mounted stent was tested for securement force using a validated test method. FIG. 1 shows a scatter plot of the securement improvement of the water-soaked units over the non-soaked units.

After securement testing the stent was removed by hand from the balloon of one sample each of the control and invention balloons, and the two balloons were photographed. FIG. 2 shows comparison photo images of both balloons after the stent was removed. The unsoaked control balloon A is at the top and the soaked invention balloon B at the bottom. It can be readily seen that there was substantially more pillowing of the balloon wall surface on the invention balloon relative to the control balloon.

Separate tests run on similar catheter designs have demonstrated that a balloon burst property was not affected by a plasticization process substantially as described in the Example herein.

The results of wet balloon crimping at room temperature were substantially equivalent to dry balloon crimping at high temperatures. As a result of the inventive method, the stent is less likely to move out of its position on the catheter during delivery or become separated from the catheter within a body vessel.

The pillowing of balloon B in FIG. 2 is similar to that obtained with prior heating techniques. However, because no heating is needed in the crimping step, the invention can be used even when highly heat sensitive substances are present. This is particularly beneficial for drug-coated stents where the level of heat needed to improve securement may negatively impact the drug coating.

Without being bound thereby, it is hypothesized that water molecules diffuse into the balloon amorphous domains and form hydrogen bonds with amide segments to replace hydrogen bonds between amide segments themselves. This reduces inter-chain interaction in the manner of a classic plasticizer. The reduced inter-chain interaction enhances the individual amorphous polymer chain's mobility, softening the material. Accordingly, other compounds or combinations of compounds, that can interfere with inter-chain polymer interactions without dissolving the polymer and that can then be removed by volatilization, can be employed.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from a antecedent-possessing claim other than the specific claim listed in such dependent claim below.

The invention claimed is:

1. An assembly comprising a catheter, a deflated balloon mounted on the catheter and a stent mounted over the balloon, wherein the balloon comprises polymer material having a fugitive plasticizer distributed therein, the polymer material comprises a polymer that forms inter-chain hydrogen bonds and the fugitive plasticizer comprises a polar organic compound.

2. An assembly as in claim 1 wherein the fugitive plasticizer is a compound that is a liquid at ambient temperature and pressure and has a boiling point at standard pressure of from about 95° C. to about 200° C.

3. An assembly as in claim 1 wherein the polymer material comprises a polyamide, a polyurethane, a polyester, a block copolymer having at least one polyamide block, a block copolymer having at least one polyester block or a block copolymer having at least one polyurethane block.

4. An assembly as in claim 3 wherein the polymer material is a polyamide/polyether block copolymer.

5. An assembly as in claim 1 wherein the fugitive plasticizer is absorbed into the balloon material without substantial swelling thereof.

6. An assembly as in claim 5 wherein the fugitive plasticizer is present in an amount of from 0.1 to 10% by weight.

7. An assembly as in claim 1 wherein the fugitive plasticizer does not swell the volume of the balloon material by more than 5%.

8. As assembly as in claim 1 wherein the fugitive plasticizer is present in a saturation amount.

9. An assembly as in claim 1 wherein the fugitive plasticizer softens the balloon polymer material, and the stent has been mounted on the balloon while the balloon was in said softened state, without pressurization of the balloon or heating the balloon above a limiting temperature of 50° C.

10. An assembly as in claim 9 wherein said limiting temperature is 37° C.

11. An assembly as in claim 1 wherein from the time the stent is crimped and while the fugitive plasticizer remains in the balloon the balloon is not heated above a limiting temperature of 50° C.

12. An assembly as in claim 1 wherein the amount of fugitive plasticizer incorporated into the balloon polymer material is an amount that is effective to soften the polymer.

13. An assembly comprising a catheter, a deflated balloon mounted on the catheter and a stent mounted over the balloon, wherein the balloon comprises polymer material having a fugitive plasticizer distributed therein and the fugitive plasticizer is a compound or mixture of compounds that can solubilize the polymer only at elevated temperatures above about 120° C., but functions as a fugitive plasticizer at ambient temperature.

14. An assembly comprising a catheter, a deflated balloon mounted on the catheter and a stent mounted over the balloon, wherein the balloon comprises polymer material having a fugitive plasticizer distributed therein, and wherein the fugitive plasticizer is a member of the group consisting of polyhydric alcohols; mono- and di-alkyl glycol ethers; acetate esters of glycol monoalkyl ethers; isophorone; benzyl alcohol; 3-methoxybutanol-1; 3-methoxybutanol-3; ethylene carbonate; propylene carbonate; phenylglycol ethers; 2,2,4-trimethyl-1,3-pentanediolmonoisobutyrate; phenols; dihydroxybenzenes; and mixtures of two or more thereof.

15. An assembly comprising a catheter, a deflated balloon mounted on the catheter and a stent with sidewall openings therethrough crimped over the balloon, the stent having a coating comprising a drug, wherein the stent has been crimped on the balloon while the balloon was in a softened state using a fugitive plasticizer to produce a pillowing of the balloon material between sidewall openings in the stent, said pillowing having been produced without exposing the drug coating to a limiting temperature in excess of 50° C. or exposing the balloon material to a solvent therefor.

16. An assembly as in claim 15 wherein the drug coating has not been exposed to a temperature above ambient temperature.

17. An assembly as in claim 15 wherein the drug coating comprises paclitaxel.

18. An assembly as in claim 15 wherein said limiting temperature is 37° C.

19. An assembly comprising a catheter, a deflated balloon mounted on the catheter and a stent with sidewall openings therethrough mounted over the balloon, wherein the assembly was formed by crimping the stent on the balloon while the balloon was in a softened state to produce a pillowing of the balloon material between sidewall openings in the stent, said softened state having been provided by incorporation of a fugitive plasticizer into the balloon material without substantial swelling thereof, while the balloon was in said softened state the balloon was not pressurized, and said fugitive plasticizer was subsequently substantially removed, leaving an ambient equilibrated amount of fugitive plasticizer remains in the polymer material after extended equilibration at ambient temperature, humidity and pressure.

20. An assembly as in claim 19 wherein while the balloon was in said softened state the balloon was not heated above a limiting temperature of 50° C.

21. An assembly as in claim 20 wherein said limiting temperature is 37° C.

* * * * *